(12) United States Patent
Novak et al.

(10) Patent No.: US 6,403,329 B1
(45) Date of Patent: Jun. 11, 2002

(54) METHODS OF DETECTING METHYLPHOSPHONIC COMPOUNDS

(75) Inventors: Thaddeus John Novak, Bel Air; Herbert Samuel Aaron, Baltimore; Tracey Denise Biggs, Abingdon, all of MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/548,665

(22) Filed: Apr. 13, 2000

(51) Int. Cl.[7] .................................................. C12Q 1/46
(52) U.S. Cl. ........................................ 435/20; 435/69.2
(58) Field of Search .......................... 435/20, 69.2, 196

(56) References Cited

U.S. PATENT DOCUMENTS

| | | | | |
|---|---|---|---|---|
| 4,411,989 A | * | 10/1983 | Grow | 435/20 |
| 5,935,862 A | * | 8/1999 | Novak | 436/104 |

FOREIGN PATENT DOCUMENTS

| | | | |
|---|---|---|---|
| CS | 285242 | * | 6/1999 |

OTHER PUBLICATIONS

Jortani S. The Role of the Clinical Laboratory in Managing Chemical or Biological Terrorism. Clinical Chemistry 46(12)1883–1893, 2000.*
Novak T. Decomposition at 90 degrees C. of the Cholinesterase Substrate Indoxyl Acetate Impregnanted on Paper Supports. Analytical Chemistry 51(8)1271–5, Jul. 1979.*

* cited by examiner

Primary Examiner—Ralph Gitomer
(74) Attorney, Agent, or Firm—Ulysses John Biffoni; William W. Randolph

(57) ABSTRACT

Methods and apparatus are disclosed for screening chemical samples to detect the presence of chemical warfare agents, chemical warfare agent precursors and degradation products formed therefrom. Particular applications include detection of the presence of a cholinesterase inhibitor derived from alkyloxy methylphosphonic acids, methylphosphonic acid, and methylphosphonofluoridic acid.

12 Claims, 2 Drawing Sheets

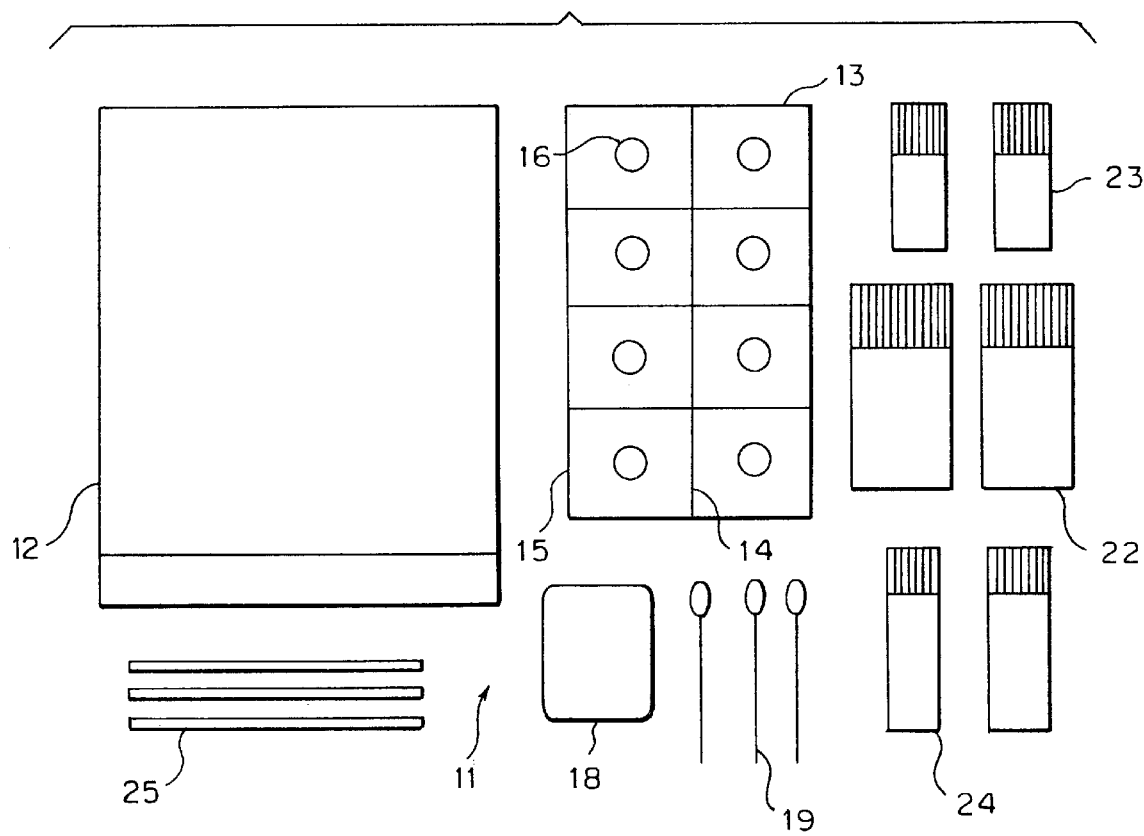
FIG.1
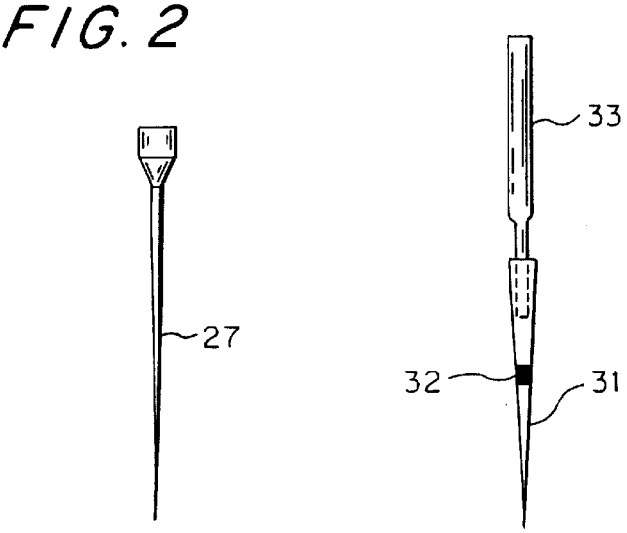
FIG.2
FIG.3

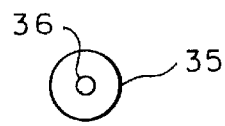
FIG. 4
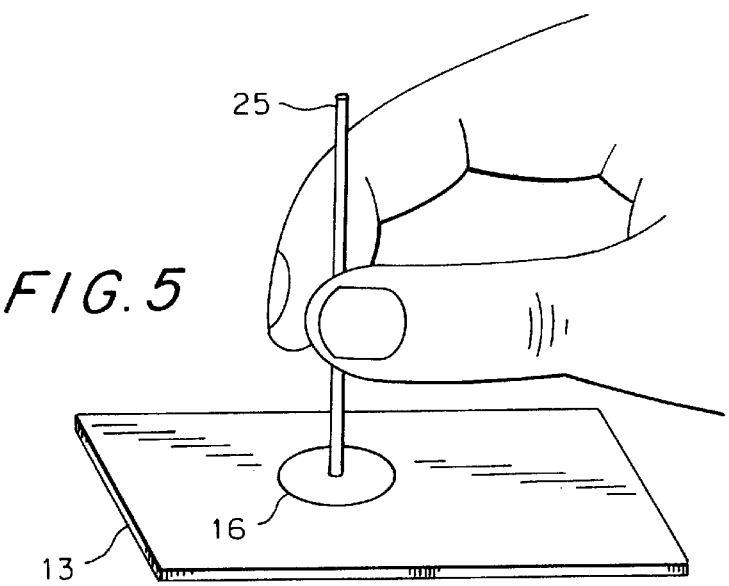
FIG. 5
FIG. 6
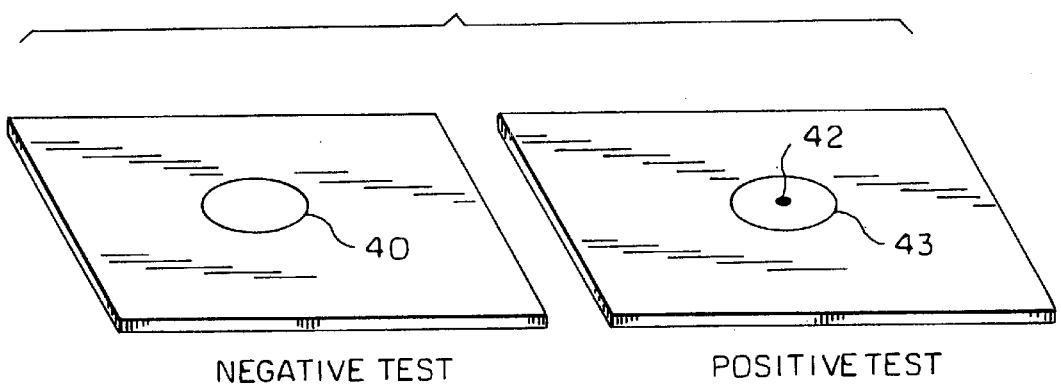
NEGATIVE TEST        POSITIVE TEST

METHODS OF DETECTING METHYLPHOSPHONIC COMPOUNDS

GOVERNMENT INTEREST

The invention described herein may be manufactured, licensed, and used by or for the U.S. Government.

BACKGROUND OF THE INVENTION

1. Field of the Invention

This invention relates to methods and kits for detecting the presence of chemical warfare agents and degradation products thereof. More particularly, the invention relates to an accurate and rapid method of detecting the presence of chemical warfare agents, precursors of chemical warfare agents, and degradation products of chemical warfare agents in a sample.

2. Description of the Prior Art

Over the years, various highly toxic chemical warfare agents (CWA's) have been developed and stockpiled by several nations. In view of the health hazards associated with CWA's and degradation products thereof, a Chemical Weapons Convention (CWC) has been developed by certain countries. The CWC monitors, detects and identifies and, if necessary, disposes of CWA's which are not in compliance with the convention. As a result of the convention, it is often necessary to conduct inspections of various sites in order to assure compliance.

On-site analysis of sample unknowns in CWC verification inspections is preferred to off-site analysis. Some reasons for this preference include:

a) existing agreements call for on-site analysis;

b) when samples are analyzed on-site, ambiguities can be resolved during the inspection;

c) since unknown samples are not removed from the inspection site, contamination and cross-contamination of samples during travel to off-site laboratories cannot occur; and d) since ambiguities will be resolved on-site during the inspection, the inspection report that is completed at the end of the inspection would not be subject to challenge.

One of the requirements for the screening methods employed in on-site inspections is that they be essentially non-intrusive. Every possible effort must be made to utilize analytical methods that do not disclose sensitive corporate or governmental information during on-site inspections. Reagent-based screening methods are attractive because many tests can be run in a short period of time and, since they give only a positive or negative response, they are capable of providing presumptive evidence for a prohibited substance in a sample without revealing the identity of any of the components in the sample.

Consequently, a number of reagent based screening tests have been included in the initial operating capability (IOC) for the on-site CWC verification inspections. Unfortunately, these tests do not have a high degree of detection specificity.

Classical spot tests are usually carried out in a porcelain spot plate containing depressions to which detector reagents are added. In practice, a small amount of a test sample, hereinafter, "a sample unknown" is placed in one or more of the depressions of the spot plate. Small quantities of one or more reagents are then added to it. A positive test is usually signified by a color change. As many as 12 different spot tests can be carried out in a small (3.5 inch×4.5 inch) spot plate. In most cases, the lower limit of detection is in the 1–100 microgram range.

In view of the advantages of rapidly and accurately identifying the presence of CWA's and associated by-products, there is a need for rapidly and accurately detecting submicrogram quantities of CWA, CWA precursors and related degradation byproducts.

SUMMARY OF THE INVENTION

The invention provides a method of detecting the presence of chemical warfare agents, chemical warfare agent precursors and degradation products thereof, (hereinafter "analytes"). This method includes the steps of contacting a sample suspected of containing a member of the group consisting of chemical warfare agents, chemical warfare agent precursors, chemical warfare agent degradation products and mixtures thereof with a sufficient amount of a chromatographic adsorbent material and a sufficient amount of a chromogenic detector reagent, so that a chromogenic indicator is formed when the sample contains a member of the aforementioned group of chemical warfare agents. A particular application is a method for detecting the presence of an alkyloxy methylphosphonic acid, comprising the steps of reacting the alkyloxy methylphosphonic acid with a dehydrating agent so that a cholinesterase inhibitor is produced and then detecting the presence of the cholinesterase inhibitor. Another application is a method for detecting the presence of methylphosphonic acid, comprising the steps of reacting the methylphosphonic acid with an esterification agent so that an alkyloxy methylphosphonic acid is formed, then reacting the resultant alkyloxy methylphosphonic acid with a dehydrating agent so that a cholinesterase inhibitor is formed, and then detecting the presence of the cholinesterase inhibitor. A further application is a method for detecting the presence of methylphosphonofluoridic acid, comprising the steps of reacting the methylphosphonofluoridic acid with a suitable esterification agent so that an alkyloxy methylphosphonofluoridate, a cholinesterase inhibitor, is formed, and then detecting the presence of the cholinesterase inhibitor.

Another aspect of the invention provides a kit for chromogenically detecting the presence of chemical warfare agents, chemical warfare agent precursors and degradation products thereof. The kit includes a means for obtaining a sample suspected of containing a member of the group consisting of chemical warfare agents, chemical warfare agent degradation products and mixtures thereof, chromatographic sorbent material, chromogenic detector reagents, and a means for reacting the sample on a chromatographic sorbent material with a chromogenic detector reagent so that a chromogenic indicator can be formed when the sample contains one of the aforementioned members of the group.

BRIEF DESCRIPTION OF THE INVENTION

Other objects and advantages of the invention will become apparent upon reading the following detailed description with reference to the attached drawings, wherein:

FIG. 1 is a plan view of a field test kit for performing on-site chemical analysis;

FIG. 2 is a plan view of a pipet with a micro-tip;

FIG. 3 is a plan view of a removable micropipet tip;

FIG. 4 is a view of the end portion of a capillary tube;

FIG. 5 is a view generally showing the end portion of a capillary tube in contact with a sorbent layer; and FIG. 6 is a plan view of a sorbent layer depicting the results of a micro spot test.

DETAILED DESCRIPTION OF THE PREFERRED EMBODIMENT

As set forth in U.S. Pat. No. 5,935,862 issued Aug. 10, 1999 to Thaddeus J. Novak and incorporated by reference, the micro spot system and methodology of detecting the presence of target analytes in a sample comprises the application of a solution containing the analytes to a chromatographic sorbent material by capillary action and adding a sufficient amount of a chromogenic detector reagent to form a chromogenic indicator when a target analyte is present in the sample. A particular application provides a method of detecting the presence of chemical warfare agents, chemical warfare agent precursors and degradation products thereof which comprises contacting a sample suspected of containing a member of the group consisting of chemical warfare agents, chemical warfare agent precursors, chemical warfare agent degradation products and mixtures thereof with a sufficient amount of a chromatographic sorbent material and a sufficient amount of a chromogenic detector reagent, whereby a chromogenic indicator is formed when a sample contains a member or analyte of the group. A further provision includes combining an aqueous sample suspected of containing the CWA analyte with an immiscible solvent which is capable of extracting the CWA analyte believed to be therein in order to obtain a sample solution for the test.

Apparatus for accomplishing this is generally shown in FIG. 1. In FIG. 1, the apparatus or kit 11 includes a bag or container 12 for storing the components of the system; at least one thin layer chromatographic plate or TLC plate 13; collecting devices such as cloth wipes 18 or swabs 19 for wiping surfaces for chemical residues; solvent containers 22; containers 23 for receiving the swabs and solvent solutions; reagent containers 24; and small diameter capillary or microcapillary tubes 25. A system or kit 11 for on-site detection and screening of a broad array of both volatile and non-volatile chemicals normally includes a wide variety of chemical reagents preferably stored in dry condition and in an inert atmosphere in small 2 to 3 ml sealed containers or bottles 24, as represented in FIG. 1. Solvents for the samples and the reagents are stored in separate bottles 22. In use, the solvent is added to dissolve the reagent in the bottle in which it was stored or in a separate container shortly prior to use. To insure a long shelf-life stability, the solid state reagents are preferably stored in dry condition, in an atmosphere that is free of moisture, and in which air has been displaced by an inert gas such as nitrogen or argon.

For purposes of this application, the term sample is defined as a representative fraction of the material that is to be processed and tested to detect the presence of an analyte. The sample may be a solid, such as soil, a liquid, such as water taken from a lake, or a vapor, such as fumes obtained from a chemical plant. An analyte is a chemical substance present in the samples that are being tested or analyzed. A solution is a homogeneous liquid that contains dissolved chemical substances. The analyte is a solute, which is defined as a chemical substance or mixture of chemical substances that dissolves in a solvent or a mixture of solvents to form a solution. A sample solution is a homogeneous liquid that contains dissolved chemical substances (i.e., the analytes or solutes) and which is derived by washing, extracting, or eluting a sample with a solvent or mixture of solvents. For example, surface wipes 18 or swabs 19 of polyester or similar material are used to obtain a sample by wiping a suspected surface. A sample solution is obtained for analysis by washing, extracting or eluting the wipe in a container 23 with a suitable solvent such as acetone, dichloromethane, hexane, etc. Soil samples can be washed, extracted or eluted in separate containers to obtain sample solutions. Aqueous samples suspected of containing a target analyte can be extracted with an immiscible solvent which is capable of extracting the analytes believed to be therein. In addition, solid phase extraction (SPE) or solid phase microextraction (SPME) techniques can be used to extract analytes from water for analysis using the micro spot tests.

Once the solution or liquid extract has been formed, and where necessary the extract has been concentrated by evaporation, a tube with a small diameter bore or opening 25, such as a small diameter capillary or microcapillary tube is used to collect and dispense small amounts of the solution onto the surface of plate 13 by capillary action. Preferably, the plates 13 are thin layer chromatographic plates or TLC plates having a surface layer formed of a chromatographic sorbent material. A sorbent material is a material that has both absorption and adsorption characteristics. Absorption is defined as the penetration of liquids into the bulk of a porous material somewhat like a sponge soaking up water. Adsorption is a process whereby a chemical substance, an analyte, sticks, clings or adheres to the surface of a solid constituent, the adsorbent. In FIG. 1, the plates have been provided with scoring lines 14 to divide the plate 13 into a plurality of separate sections 15 that serve as different test sites. Generally, the amount of sample delivered to a test site on the chromatographic material from a microcapillary tube having a length of one and one quarter inches is on the order of from about 0.1 microliters (for an approximate 0.05 mm diameter microcapillary opening) to about 30 microliters (for an approximate 1.6 mm diameter microcapillary opening) of sample. In most instances sample size will be on the order of from about 0.5 microliters (for an approximate 0.1 mm diameter microcapillary opening) to about 5 microliters (for an approximate 0.4 mm diameter microcapillary opening) and preferably, the sample will be on the order of from about 1 microliter (for an estimated 0.2 mm diameter microcapillary opening) to about 3 microliters (for an estimated 0.25 mm diameter microcap opening). Microcapillary tubes having longer lengths can be used. If desired, the microcapillary tube 25 can be held with commercially available holders or forceps.

The term "microcapillary tube" includes any tube made from glass, plastic or other material having a small diameter opening that is capable of dispensing liquid from (or drawing liquid into) the opening by capillary action. Examples of small diameter capillary tubes are those marketed by Drummond and sold under the trademarked name of Microcaps. Another type of tube having a small diameter opening is a micropipet. A micropipet is a glass or plastic tube having a small diameter opening (or capillary opening) at one end and an enlarged opening at the other end of the micropipet, as generally shown by micropipet 27 in FIG. 2. Examples of micropipets are Micro-tip polyethylene pipets sold by Micro Mole Scientific. One benefit of a micropipet is that if the top of the bulb is cut off, as shown in FIG. 2, the larger end functions as a funnel for holding a larger volume of fluid sample than could normally be held or drawn into a capillary tube. Consequently, a larger volume of sample (such as 10 microliters or more) can be used to achieve better detection sensitivity with respect to the concentration of analyte that can be detected. Replaceable micropipet tips 31, as shown in FIG. 3, are examples of additional devices that have small diameter openings. A removable micropipet tip 31 would be placed on the end portion of another tube 33 or container so that the liquid in the tube or container would be withdrawn by capillary action when placed in contact with a chromatographic sorbent material. An additional deposition control could be achieved by use of an in-line filter element 32 in a microcapillary device. One example of a micropipet tip is available under the tradename of Plastibrand autoclavable nonsealing filter tips and another example of a micropipet tip without a filter is Catalog No. 71-6311-10 from PGC Scientific, Gaithersburg, Md. An example of a micropipet tip with a filter is Catalog No. 71-6311-16 from PGC Scientific, Gaithersburg, Md. While microcapillary tubes, micropipets and micropipet tips have been distributed for use with bulbs or other devices for forcing liquid out of the tubes, use of such pressure devices for forcing liquid from microcapillary tubes is contrary to the methodology of the present invention where the solution containing the analyte is deposited by capillary action. Further, while some methodologies for applying a sample to a TLC plate includes spreading the sample across the TLC plate, use of such methodology of moving the tip of the microcapillary tube across the TLC plate is contrary to the methodology of the present invention where all of the analyte contained in the sample solution should be adsorbed at a fixed location, in the smallest volume of sorbent.

To avoid the possibility of the analyst being contaminated with the sample solution as a result of breaking extremely thin microcapillary tubes, micropipets and micropipet tips during use when the ends portions of these devices contact sorbent surfaces, it is possible to use various holding devices such as forceps and small clamps. While microcapillary tubes have been found acceptable for most applications, where conditions or technique warrant, the end portions of the tubes can be formed with thickened wall portions as shown in FIG. 4, where the thickness of the wall portions 35 are at least equal to the diameter of the opening 36 of the tube 25. Increasing the wall thickness to at least twice the diameter of the opening not only strengthens the end portion of the tubes for adverse use conditions, but also provides a larger contact surface area relative to the size of the opening and thereby promotes higher circumferential contact and seal of the microcapillary tubes with the sorbent material.

The chromatographic adsorbent material is preferably a thin-layer chromatography (TLC) plate such as those commonly found in the art containing a silica gel, glass backed thin layer chromatography sheet. A non-limiting list of suitable TLC strips which can be used in carrying out the invention include MK6F Silica Gel 60A TLC plates, glass backed (1 inch×3 inch plates), layer thickness 250 microns, Cat. #4861-110 from Whatman, Inc., Clifton, N.J. 07014; Silica Gel F-254 TLC media, plastic backed, layer thickness 0.25 mm, Cat #5775 from E.M. Laboratories, Elmsford, N.Y. 10523; Silica Gel F-254 TLC media, aluminum backed, layer thickness 0.2 mm, Cat #5539 from Alltech Associates, Deerfield, Ill. 60115; Silica Gel TLC media, plastic backed, layer thickness 100 microns, Product Number 13179, Cat. #4G 6801, Eastman Kodak Co., Rochester, N.Y. 14650; Instant Thin Layer Chromatography Polysilicic Acid Gel Impregnated Glass Fiber Sheets with Fluorescent Indicator, Product Number 51435, Gelman Instruments, Ann Arbor, Mich. 48106; Instant Thin Layer Chromatography Sheets, Type SG, Product Number 61886, Gelman Instrument Co., Ann Arbor, Mich. 48106; TLC Plates, Silica Gel 60 F-254, aluminum backed, layer thickness 0.2 mm, Product #37360, Catalog #Z19,329-1, Aldrich Chemical Co., Milwaukee, Wis. 53233; Silica Gel IB Flexible (plastic backed) Sheets for Thin Layer Chromatography, layer thickness 250 microns, Product Number 4462-02, J. T. Baker, Inc., Phillipsburg, N.J. 08865; Aluminum Oxide IB Flexible (plastic backed) Sheets for Thin Layer Chromatography, layer thickness 200 microns, Product Number 4466-00, J. T. Baker, Inc., Phillipsburg, N.J. 08865; MKC18F Reversed Phase TLC plates, glass backed (1 inch×3 inch plates), layer thickness 200 microns, Cat. #4803-110 from Whatman, Inc., Clifton, N.J. 07014.

Preferably, the sorbent layer of the TLC medium to which the sample solution is applied with a microcap should be capable of acting both as an adsorbent and as an absorbent. It is believed that when the sample solution, which contains an analyte (i.e., the solute) dissolved in a solvent, is applied to the sorbent by capillary action using a microcapillary device, the solute separates from the solution because it adheres or clings to the walls of the pores in a small volume of the sorbent immediately surrounding the point of application of the sample solution due to adsorption, while the solvent, a fluid which consequently has been freed from the solute, fills the voids in the pores of the sorbent due to absorption. This phenomenon results in the analyte concentrating within the sorbent layer and being localized in a small volume of the sorbent or "spot", while the solvent freely wets a substantial volume of sorbent. Since the volume of sorbent in which the solute is adsorbed is a small fraction of the volume in which the solvent is absorbed, the analyte becomes highly concentrated and consequently, high sensitivity of detection is made possible in the micro spot tests. When the analyte is present in very low concentration levels, application of the sample solution to the sorbent layer will result in the analyte concentrating in a very small volume of sorbent, and hence, will produce only a very small spot. Whereas, if the analyte is present in a somewhat higher concentration level, application of the sample solution to the sorbent layer will result in the analyte concentrating in a somewhat larger volume of sorbent, and hence, will produce a somewhat larger spot. FIG. 5 depicts a view where the end portion of a microcapillary tube has been placed in sufficient contact with a sorbent layer so that as the solution containing the analyte leaves the opening in the end portion of the tube, the analyte is adsorbed in a small localized region or spot about the point where the tip or end of the microcapillary tube contacts the sorbent layer, while the solvent spreads throughout the porous medium as it wets and is absorbed into the sorbent layer.

After a period of about 1 minute, the combination of the sample and the chromatographic adsorbent material is treated with a sufficient amount of a chromogenic detector reagent such as bromcresol green, 7,7,8,8-tetracyanoquinodimethane (TCNQ), gold chloride (without NaOH), gold chloride/NaOH solution [The slash between the reagents indicates that the reagent following the slash is used in a separate step], 4-(4'-nitrobenzyl)pyridine/NaOH, cholinesterase/indoxyl acetate, sodium pyrophosphate peroxide/aromatic amine, o-dianisidine/sodium perborate, potassium bismuth iodide, 1,3-diisonitrosoacetone guanidinium salt, bis(diethylamino)benzophenone oxime, bis (diethylamino)benzophenone, bis(dimethylamino) thiobenzophenone, phenylazoformic acid 2-diphenylhydrazide, diphenylcarbazone, diphenylthiocarbazone, mercuric salt, diethyldithiocarbamic acid silver salt, 2, 2'-dithiobis(5-nitropyridine), molybdenum oxide in sulfuric acid, ammonium molybdate, iodine/starch, and sulfuric acid (4M). This is only a non-limiting partial list of reagents that can be used in the process described herein. In some cases, it may be necessary to react the analyte deposited on the TLC medium with another reagent prior to the reaction with the chromogenic detector reagent(s). It is expected that one drop of the detector reagent(s) will be sufficient in order to obtain a result. In tests where two detector reagents are added in sequence, the second detector reagent should be added about two minutes (or more) after the first reagent. In some tests heat is used to accelerate the reaction of a detector reagent with the analyte. If the test is positive, a small spot within the reagent spot on the TLC sheet changes color, often instantaneously, but with low analyte levels may require 15–30 seconds. Furthermore, since the level of analyte appears to be related directly to the size of the color change within the spot, quantification of the analyte levels may be possible. The color changes are visible when most of the analytes are detected at the 10 nanogram (ng) level. One of the analytes can also be detected at the 1 ng level.

FIG. 6 is a plan view of a sorbent layer depicting how the results of a microspot test may appear after a detector reagent has been added to the surface of a sorbent layer. The two circular spots or regions 40 and 42 are generally representative of where the detector reagent solution has been added to a sorbent layer. The spot 40 to the left represents the results when a negative result is produced (no analyte is present) and the spot 42 to the right represents the results when a positive result is produced (an analyte is present, producing a chromogenic indication). The right spot 42 is shown to contain a smaller spot or point 43 in the center of the detector reagent spot to represent that the unknown has been localized about the point where the microcapillary tube contacts the sorbent material. While there may be some expansion of the spot relative to the size of the opening, such as would occur with a relatively high concentration of analyte or use of different solvents, the analyte generally remains concentrated at the identified spot of deposition. It was found that detection sensitivity can be improved by an order of magnitude or greater if the sample unknown is dissolved in an appropriate solvent and then applied to a small piece of thin-layer chromatography media using a microcapillary tube. Thus, for purposes of the present invention, the methods of the present invention are referred to as "micro spot tests" due to the minute quantities of analyte that are detectable compared with spot tests carried out using the techniques of the prior art. Indeed, the methods of the present invention are capable of detecting the presence of chemical warfare agents or degradation products thereof in the 1–100 nanogram range. An illustrative manner of carrying out the methods of the present invention is provided below:

A sample suspected of containing the analyte methylphosphonic acid is prepared by forming an acetone eluate from a polyester wipe. A microcapillary tube is used to draw up about 1 microliter of the sample and the end of the capillary tube is touched to a piece of TLC medium. The analyte solution wetted the adsorbent layer and migrated by capillary action. Afterward, the TLC medium was allowed to dry and a drop of Bromcresol Green reagent was added. This caused a small yellow spot to be produced in a large dark blue spot (background). This indicated that all of the acid was retained within the inner circle. The acid is retained near the spotting point due to its strong interaction with the chromatographic adsorbent. Since the analyte collects in a small area near the spotting point when the method of the present invention is used, it is possible to detect minute quantities of the analyte. In order to concentrate the analyte in the most compact spot, the solution of the analyte must exit from the microcap, and in doing so, contact only the surface of the thin-layer chromatographic media that comes in contact with the tip of the microcap. When this technique is used, the analyte solution will exit from the microcap by capillary action.

If the microcap is not kept in contact with the surface of the chromatographic media, a droplet larger than the diameter of the microcap may form. When a droplet larger than the diameter of the microcap forms and then comes in contact with the thin-layer chromatographic media, the solution will wet a large area and the analyte will not concentrate in a compact spot. Consequently, the detection sensitivity of the test will be poorer than that obtained using the method described in the previous paragraph.

Table 1 contains a list of compounds that are a representative of the Priority 1 Analytes which can be detected by the processes of the present invention. This list represents a number of analytes which would be expected to be found in an on-site CWC verification inspection. It will be understood by those of ordinary skill in the art that those analytes not specifically mentioned but known are also included herewith and that the new analyses for these analytes would be handled in the same way as analytes that are listed.

TABLE 1

PRIORITY 1 ANALYTES

| COMPOUND | SYNONYM |
| --- | --- |
| ethyl N,N-dimethylphosphoramidocyanidate | CA |
| isopropyl methylphosphonofluoridate | GB |
| pinacolyl methylphosphonofluoridate | GD |
| cyclohexyl methylphosphonofluoridate | GF |
| O-ethyl S-(2-diisopropylamino)ethyl methylphosphonothiolate | VX |
| bis(2-chloroethyl)sulfide | HD |
| bis[2-(2-chloroethylthio)ethyl]ether | T |
| 2-chlorovinyldichloroarsine | L |
| methylphosphonic difluoride | DF |
| ethyl 2-(diisopropylamino)ethyl methylphosphonite | QL |
| isopropyl methylphosphonic acid | IMPA |
| pinacolyl methylphosphonic acid | PMPA |
| cyclohexyl methylphosphonic acid | CMPA |
| methylphosphonofluoridic acid | MPFA |
| methylphosphonic dichloride | DC |
| S-(2-diisopropylamino)ethyl methylphosphonothioic acid | EA 2192 |
| ethyl methylphosphonic acid | EMPA |
| O-ethyl methylphosphonothioic acid | EMPTA |
| 1,4-dithiane | DITHIANE |
| 2-chlorovinylarsenious oxide | L-OXIDE |
| methylphosphonic acid | MPA |

In another aspect of the invention, there is provided a method wherein by using two or more micro spot tests in combination, a more specific indication of the analyte found in a sample unknown can be determined. In addition, by using a series of spot tests, the artisan is able to accumulate evidence for or against the presence of a Priority 1 Analyte in the sample without actually identifying any of the components of the sample. This is important because the acceptance of the on-site screening procedures by the chemical industry will ultimately depend on using methodology that minimizes or eliminates the need for subjecting samples unnecessarily to sophisticated, and potentially more intrusive, analytical methods.

If a sample unknown gives positive tests for one or more Priority 1 Analytes, TLCs could be run to determine if the suspect sample is a mixture, and to obtain $R_f$ value(s) of the suspect analyte(s). For example, the TLC data can show the relative positions (from which $R_f$ values are obtained) for spots resulting from, for example, multiple phosphonic acids and dithiane. The data can be obtained using a procedure similar to that developed by Sass and Ludemann for the separation of phosphonic acids, see *J. of Chromatography*, 187, 447–452 (1980), the contents of which are incorporated herein by reference. It is also noteworthy to mention that the shape of a spot on the TLCs and the rate at which the spot becomes colored when contacted by the visualizing reagent may also help to indicate which analyte is present. For example, a characteristic of the EMPTA spot is that it produces spots that have a long tail. Another characteristic of the EMPTA spot is that it changes color, going rapidly form colorless to brown when the TLC is exposed to iodine vapor. While the spot test data and the TLC data together are not sufficient to identify the components of the unknown sample, which nonetheless is a desirable feature for the screening tests, it is clear that the methods of the present invention can provide a considerable amount of evidence for the presence (or absence) of Priority 1 Analytes in a suspect sample.

Table 2 contains data that show how three of the micro spot tests can be used in combination to accumulate presumptive evidence for the presence of several different Priority 1 Analytes. TLC data can also be used in combination with the micro spot tests to supplement the spot test data and further improve detection specificity. The sample unknown for the micro spot tests is one that would contain one of the following Priority 1 Analytes: MPA, EMPA, IMPA, PMPA, EMPTA and dithiane.

The data in Table 2 indicate that the response patterns from the three different spot tests can be used to distinguish dithiane and EMPTA from each other, and from MPA and several alkyloxy methylphosphonic acids that are also Priority 1 Analytes. A positive test result in the Bromcresol Green Test indicates that an acidic substance, which could be MPA, or one or more alkyloxy methylphosphonic acids, is in the sample. If the positive test with Bromcresol Green is combined with positive tests with TCNQ (7,7,8,8-tetracyanoquinodimethane) and gold chloride/NaOH, the response pattern indicates that EMPTA may be present, but not dithiane, MPA or the alkyloxy methylphosphonic acids. A positive test with Bromcresol Green in combination with negative tests with TCNQ and gold chloride/NaOH indicates that a sample might contain MPA or one or more alkyloxy methylphosphonic acids, but not EMPTA or dithiane. Negative tests with Bromcresol Green and TCNQ combined with a positive gold chloride/NaOH test indicate that the sample may contain dithiane, but none of the phosphorus acids. Detection specificity is further improved when two or more tests are used in combination because different tests for the same analyte have different interference profiles.

TABLE 2

Results of Micro Spot Tests for Some Priority 1 Analytes
Reagent(s) for Micro Spot Test

| | Bromcresol Green | TCNQ | Gold Chloride/NaOH |
|---|---|---|---|
| Analyte | | | |
| MPA | + | − | − |
| EMPA | + | − | − |
| IMPA | + | − | − |
| PMPA | + | − | − |
| EMPTA | + | + | + |
| DITHIANE | − | − | + |

+ indicates a positive test
− indicates a negative test

Without additional data from other tests, however, the three spot tests used to obtain the data for Table 2 will not indicate if the unknown is a single substance or a mixture, and they will not indicate which phosphorus-containing acids may be present in the sample. Thus, TLC could be employed to provide more definitive results.

In another aspect of the invention there is provided a micro spot test for determining the presence of alkyloxy methylphosphonic acids. The method depends upon first converting the phosphonic acid into a cholinesterase inhibitor (CI) and thereafter using an existing test to determine if a cholinesterase inhibitor was formed in the conversion reaction. One such existing test for determining the presence of a cholinesterase inhibitor is found in the U.S. Army M-272 Detector Kit for water borne chemical agents. Another example of a test for determining the presence of a cholinesterase inhibitor is set forth in PCT International Publication WO94/05808 published Mar. 17, 1994, filed by Oritest S. S. R. O. and is incorporated herein by reference.

The procedure involves a reaction of an alkyloxy methylphosphonic acid, a non-inhibitor, with a dehydrating agent, [e.g., for example 1,3-dicyclohexylcarbodiimide or 1,3-diisopropylcarbodiimide], which causes the elimination of a molecule of water from two molecules of the acid [or alternately, the procedure can involve reaction of an alkyloxy methylphosphonic acid with an acid chloride and base (e.g., alkyloxy methylphosphonochloridate and triethylamine), which causes the elimination of a molecule of HCl], and thereby produces an acid anhydride or "pyro acid" which is a cholinesterase inhibitor and which can be detected. For example, the nerve agent detector ticket from the U.S. Army M-272 Detector Kit for Waterborne Chemical Agents is then used to determine if a cholinesterase inhibitor was formed in the reaction. This is done by placing the portion of the detector ticket that contains cholinesterase in contact with the portion of the TLC strip that contains the product of the reaction for a 3-minute period, and then proceeding with the normal procedure for tests with the M-272 detector ticket. The foregoing method is able to provide a detection sensitivity of from about 100 ng to 40 micrograms, depending on which phosphonic acid is present in the sample.

The following non-limiting examples serve to illustrate the invention.

EXAMPLE 1

Micro Spot Test for Methylphosphonic Acids Using Bromocresol Green

Detection Principle

A positive test is the appearance of a yellow spot in a larger blue spot. The control (analyte level=0) and negative tests are indicated by a blue spot that does not contain a yellow center. The color change that is observed in a positive test is due to the difference in the pH of the analyte (pH 3 and above) and the solid support (pH >5). At pH 3.8 and below, bromcresol green is yellow, and at pH 5.4 and above it is blue. The method described herein could be used for detecting other organic acids as well.

Detector Reagent:

Bromcresol Green (0.04% in ethanol).

Procedure for Preparing the Detector Reagent:

The bromocresol green reagent is available from Aldrich Chemical Company. Transfer 2 ml of the reagent into a 3-ml plastic dropping bottle, replace the tip and screw on the cover.

Solvent for the Analyte:

An organic solvent (e.g. acetone, dichloromethane, hexane)

Preferred Solid Support:

MK6F Silica Gel 60A Glass Backed TLC Sheets, Clifton, N.J.

Analytes Detected with this Test:

methylphosphonic acid (MPA), methylphosphonofluoridic acid (MPFA), ethyl methylphosphonic acid (EMPA), isopropyl methylphosphonic acid (IMPA), pinacolyl methylphosphonic acid (PMPA), cyclohexyl methylphosphonic acid (CMPA), O-ethyl methylphosphonothioic acid (EMPTA).

Detection Limit for CWC Analytes:

MPA, EMPA, IMPA, PMPA, CMPA, EMPTA, and MPFA are detectable at the 100 ng level (i.e. when a 1 microliter aliquot of an acetone solution containing 0.01%, or more of analyte is spotted on preferred solid support using a microcapillary tube).

EMPA, IMPA, CMPA, PMPA and EMPTA are also detectable at the 10 ng level (i.e. when a 1 microliter aliquot of a dichloromethane solution containing 0.001% or more of analyte is spotted on the preferred solid support using a microcap).

Equipment and Materials:
  a. Locking forceps or spotting bulb assembly for holding microcap (e.g. cat. #20-99, Analtech, Newark, Del.)
  b. Microcap, 1-microliter (e.g. cat. #20-01, Analtech)
  c. Dropping Dottle, 3-ml capacity, (e.g. cat. #211630, Wheaton, Millville, N.J.)
  d. 0.04% Bromcresol Green in Ethanol, cat. #B-7382, Sigma Chemical Co., St. Louis, Mo.)
  e. MK6F Silica Gel 60A Glass Backed TLC Sheets or equivalent (e.g. cat. #4861-110, Whatman Inc., Clifton, N.J.)
  f. Acetone (e.g. cat. #GC60032-4, Baxter Healthcare Corp., Burdick and Jackson Div., Muskegon, Mich.)
  g. Pencil Procedure 1. Score a 1 inch×3 inch TLC plate into twelve 0.5 inch×0.5 inch sections with a pencil.

2. Lock a 1-microliter microcap in the tip of the locking forceps.

3. Place tip of microcap in a sample of pure acetone (or other solvent for the test) and wait a few seconds for the solvent to be drawn by capillary action to fill the microcap.

4. Place the tip of the microcap in contact with the silica gel surface of the solid support near the center of one of the 0.5 inch×0.5 inch sections. This is the "control" (analyte level=0) spot.

5. Wait a few seconds for the solvent to evaporate.

6. Using a new microcap, for each sample, spot a different sample solution in each of the remaining 0.5 inch×0.5 inch sections of the plate and allow the solvent to evaporate.

7. Using the dropping bottle, add one (1) drop of the bromocresol green to each spot.

8. Observe the plate for the appearance of positive tests. A positive test is indicated by the appearance of a small yellow spot in a large green (wet) or blue (dry) spot. A positive detection signal appears within 1–2 seconds and the colors remain stable for at least several hours.

Purpose and Applications

This micro spot test method detects acids and can be used as a field screening test for phosphonic acids. A positive test indicates that a sample that may contain MPA, MPFA, EMPA, IMPA, CMPA, PMPA, or EMPTA. The test provides evidence for or against the presence of CWC analytes in a sample unknown. This test can be used alone or in conjunction with other micro spot tests that detect other functional groups in the sample unknown. When two or more micro spot tests are used in combination, the detection specificity for target CWC analytes is increased compared with the result of a single test.

EXAMPLE 2

Micro Spot Test for O-Ethyl Methylphosphonothioic Acid (EMPTA) Using 7,7,8,8-Tetracyanoquinodimethane (TCNQ)

Detection Principle

A positive test is the appearance of a blue spot in a larger pale yellow spot. If fresh reagent is not used, however, the reagent spot may be green instead of pale yellow. (With high analyte levels, the center of the blue spot may be bleached so that a white spot appears instead of a blue spot). The control (analyte level=0) and negative tests are indicated by a pale yellow spot that does not contain a blue spot in the center. The color change that is observed in a positive test is due to a sulfhydryl group in the analyte converting the 7,7,8,8-tetracyanoquinodimethane (TCNQ) reagent into a highly colored free radical. In a positive test, the color change occurs within 1 or 2 seconds after applying the TCNQ reagent.

Detector Reagent:

7, 7, 8,8-tetracyanoquinodimethane (2.5% in acetone)

Procedure for Preparing Detector Reagent

In a 3-ml plastic dropping bottle place 5 mg of TCNQ. Add 2 ml of acetone. Place the dropping bottle tip in place and screw on the cap. Swirl until all of the TCNQ reagent dissolves.

Solvent for the Analyte:

Acetone, dichloromethane, or hexane.

Preferred Solid Support:

MK6F Silica Gel 60A Glass Backed TLC Sheets, cat.#4861-110, Whatman Inc.

Analytes Detected with this Test

O-ethyl methylphosphonothioic acid (EMPTA) as well as other materials containing phosphonothioic acid groups, sulfhydryl groups and other TCNQ free radical precursors.

Detection Limits for CWC Analytes

EMPTA is detectable at the 10 ng level (i.e., when a 1-microliter aliquot of an acetone solution containing 0.001% or more of analyte is spotted on preferred solid supports using a microcapillary tube).

Equipment and Materials

Same as Example 1 except that 7,7,8,8-Tetracyanoquinodimethane (e.g. cat. #B-7382, Sigma Chemical Co., St. Louis, Mo.) was used instead of the Bromcresol Green.

Procedure

Same as Example 1 except that 7,7,8,8-Tetracyanoquinodimethane was used in step 7. In this example, the observation step required observing the plate for the appearance of positive tests which was indicated by the appearance of a small blue spot in a large yellow spot. The reagent spot may be green. if fresh reagent is not used. A positive detection signal appears within 1–2 seconds and the colors remain stable for at least several hours.

Purpose and Applications

This micro spot test method can be used as a field screening test for compounds containing a phosphonothioic acid group. A positive test indicates that a samples may contain EMPTA. The test provides evidence for or against the presence of CWC analytes in a sample unknown. This test can be used alone or in conjunction with other micro spot tests that detect other functional groups in the sample unknown. When two or more micro spot tests are used in combination, the detection specificity for target CWC analytes is increased compared with the result of a single test.

EXAMPLE 3

Micro Spot Test for O-Ethyl Methylphosphonothioic Acid (EMPTA), 1,4-Dithiane, Bis(2-chloroethyl)sulfide (HD), and Bis [2-(2-ethylthio)ethyl] ether (T) Using Gold Chloride and Sodium Hydroxide Detection Principle In this test, two detector reagents are added in sequence. The first reagent is an aqueous solution of gold chloride. The second reagent is an aqueous solution of sodium hydroxide. It is believed that the first reagent forms a brown complex with compounds containing a thioether, phosphonothioic acid group or a sulfhydryl group. The second reagent, aqueous sodium hydroxide, probably hydrolyzes the complex thereby forming gold hydroxide, which is unstable, and decomposes to gold oxide. A purplish black spot (gold oxide) in a yellow background signifies a positive test. This color change occurs at the location where the sample was spotted on the solid support. Small black speckles may also appear in the test spot. The small speckles, which occur randomly in the reagent spot should be ignored.

Detector Reagents
1. Aqueous 4% Gold Chloride Solution
2. Aqueous 2N Sodium Hydroxide Procedure for Preparing Detector Reagents Reagent #1; Place hydrogen tetrachloroaurate trihydrate (1 g) in a 25 ml volumetric flask and add water to the mark. Allow the solution to stand for 1 week. Place 2 ml of the solution in a 2-ml plastic dropping bottle. Replace the plastic tip and screw the cover on tightly.

Reagent #2; Place sodium hydroxide (8.0 grams) in a 100 ml volumetric flask. Add approximately 75 ml of water and swirl until the sodium hydroxide dissolves. Allow the solution to cool to room temperature. Add water to the mark.

Solvent for the Analyte:
An organic solvent (e.g. acetone, dichloromethane, hexane)

Preferred Solid Support:
MK6F Silica Gel 60A Glass Backed TLC Sheets, cat. #4861-110, Whatman Inc.

Analytes Detected with this Test
O-ethyl methylphosphonothioic acid (EMPTA), Bis(2-chloroethyl)sulfide (HD), Bis[2-(2-ethylthioethyl)]ether (T), 1,4-dithiane and other compounds containing a thioether, a phosphonothioic acid group or a sulfhydryl group.

Detection Limits for CWC Analytes
EMPTA is detectable at the 1 ng level (i.e. when a 1-microliter aliquot of a dichloromethane or hexane solution containing 0.0001% or more of analyte is spotted on the solid support using a microcap).

Dithiane is detectable at the 10 nanogram level; (i.e. when a 1-microliter aliquot of a dichloromethane or hexane solution containing 0.001% or more of the analyte is spotted on the solid support using a microcap).

Bis [2-(2-ethylthio)ethyl]ether (T) is detectable at the 10 ng level when it is applied to the thin-layer chromatographic media in hexane solution. Bis(2-chloroethyl)sulfide is detectable at the 100 ng level when it is applied to the thin-layer chromatographic media in dichloromethane solution.

Equipment and Materials
Same as those used in Example 1 except that hydrogen tetrachloroaurate (III) trihydrate (e.g. cat. #24,459-7, Aldrich Chemical Co.) and sodium hydroxide (#22146-5, Aldrich Chemical Co.) were used instead of the Bromcresol Green.

Procedure
The same first six steps of example 1 were followed. Thereafter, the steps are:

7. Using the dropping bottle, add 1 drop of the gold chloride reagent to each spot.
8. Wait two minutes. [EMPTA can be detected down to the 10 ng level at this point. Therefore, it can be distinguished from the other analytes (that require base-step 9)].
9. Using the dropping bottle, add 1 drop of the sodium hydroxide solution to each spot.
10. Observe the plate for the appearance of a positive test. A positive test is indicated by the appearance of a small purplish black spot in a large pale yellow spot. A positive detection signal appears within 1–2 seconds and the colors remain stable for at least several hours. The test spot may contain dark speckles that appear randomly and with increasing frequency as the spot ages. These should be ignored.

Purpose and Applications
This micro spot test method can be used as a field screening test for compounds containing a thioether or a phosphonothioic acid group. A positive test indicates that a sample may contain HD, T, EMPTA, or dithiane. The test provides evidence for or against the presence of CWC analytes in a sample unknown. This test can be used alone or in conjunction with other micro spot tests that detect other functional groups in the sample unknown. When two or more micro spot tests are used in combination, the detection specificity for target CWC analytes is increased compared with the result of a single test.

EXAMPLE 4

Micro Spot Test for Bis(2-chloroethyl)sulfide (HD). Bis[2-(2-ethylthio) ethyl]ether (T), and Other Mustards (Including Nitrogen Mustards) Using 4-(4'-Nitrobenzyl)pyridine and Sodium Hydroxide Detection Principle
In this test, two detector reagents are used in combination. The first reagent is a 2% solution of 4-(4'-nitrobenzyl)pyridine in an organic solvent such as denatured ethyl alcohol or toluene. The second reagent is an aqueous solution of sodium hydroxide. The thin-layer chromatographic media is heated after the 4-(4'-nitrobenzyl)pyridine is applied to the analyte spot. In the first reaction, heat accelerates the alkylation 4-(4'-nitrobenzyl)pyridine by the analyte. Basification then results in a deprotonation reaction that produces a blue dye. A positive test response is a small dark blue or purple spot on a white or pale red background.

Detector Reagents
1. 4-(4'-Nitrobenzyl)pyridine (2%) in denatured ethanol (or toluene)
2. Aqueous 2N Sodium Hydroxide Procedure for Preparing Detector Reagents
Reagent #1 Place 4-(4'-nitrobenzyl)pyridine (20 mg) in a 2-ml plastic dropping bottle. Add 1 ml of ethanol (or toluene). Swirl until the solid dissolves. Replace the plastic tip and screw the cover on tightly.

Reagent #2 Place sodium hydroxide (8.0 grams) in a 100 ml volumetric flask. Add approximately 75 ml of water and swirl until the sodium hydroxide dissolves. Allow the solution to cool to room temperature. Add water to the mark.

Solvent for the Analyte:
Acetone, dichloromethane, or hexane.

Preferred Solid Support:
MK6F Silica Gel 60A Glass Backed TLC Sheets cat #4861-110, Whatman, Inc.

Analytes Detected with this Test

Bis(2-chloroethyl)sulfide (HD), Bis[2-(2-ethylthio)ethyl] ether (T), as well as other sulfur- and nitrogen-mustards. Other alkylating agents (e.g. diethyl sulfate) will also be detected.

Detection Limits for CWC Analytes

Bis [2-ethylthio)ethyl]ether (T) is detectable at the 10 ng level when it is applied to the thin-layer chromatographic media in hexane solution. Bis(2-chloroethyl)sulfide is detectable at the 100 ng level when it is applied to the thin-layer chromatographic media in dichloromethane solution.

Equipment and Materials

Same as those used in Example 1 except that 4-(4'-nitrobenzyl)pyridine (e.g. cat. #N1,420-4, Aldrich Chemical Co.) and sodium hydroxide (#22146-5), Aldrich Chemical Co.) are used instead of bromcresol green.

Procedure

The same first six steps of Example 1 were followed. Thereafter, the steps are:

7. Using a dropping bottle, add 1 drop of the 4-(4'-nitrobenzyl)pyridine reagent.
8. Place the thin-layer chromatographic plate on a hot plate set at 90 degrees Centigrade. Wait for two minutes.
9. Remove the thin-layer chromatographic plate from the hot plate and allow it to cool for 15–30 seconds.
10. Using the dropping bottle, add 1 drop of the sodium hydroxide solution to each spot.
11. Observe the plate for the appearance of a positive test. A positive test is indicated by the appearance of a small blue or purple spot on a white or pale red background. A positive signal appears within 15 seconds and the colors remain stable for at least several hours.

Purpose and Applications

This micro spot test method can be used as a field screening test for alkylating agents. A positive test indicates that the sample may contain HD or T. The test provides evidence for or against the presence of CWC analytes in a sample unknown. This test can be used alone or in conjunction with other micro spot tests that detect other functional groups in the sample unknown. When two or more micro spot tests are used in combination, the detection specificity for target CWC analytes is increased compared with the result of a single test.

Another aspect of the invention relates to the use of a microspot test for determining the presence of alkyloxy methylphosphonic acids. The method depends upon first converting an alkyloxy methylphosphonic acid into a cholinesterase inhibitor (CI) and thereafter using an existing test to determine if a cholinesterase inhibitor or CI was formed in the conversion reaction. One such existing test for determining the presence of a CI is found in the U.S. Army M-272 Detector Kit for water borne chemical agents.

The procedure involves a reaction of an alkyloxy methylphosphonic acid (a non-inhibitor) with a dehydrating agent [e.g. 1,3-dicyclohexylcarbodiimide, 1,3-diisopropylcarbodiimide, or an acid chloride and base (e.g., alkyloxy methylphosphonochloridate and triethylamine)] which causes the elimination of a molecule of water (or HCl if an acid chloride is involved in the elimination reaction), thereby producing an acid anhydride or "pyro acid" which is a cholinesterase inhibitor and which can be detected. For example, the nerve agent detector from the U.S. Army M-272 Detector Kit for Waterborne Chemical Agents can be used to determine if a cholinesterase inhibitor was formed in the reaction. This is done by placing the portion of the detector ticket that contains cholinesterase in contact with the portion of the solid support that contains the product of the reaction for a 3-minute period, and then proceeding with the procedure for tests with the M-272 detector ticket. The foregoing method is able to provide a detection capability of from about 100 ng to 40 micrograms, depending on which alkyloxy methylphosphonic acid is present in the sample.

The following non-limiting example serves to further illustrate the invention.

EXAMPLE 5

Micro Spot Test for Alkyloxy Methylphosphonic Acids Using 1,3-Dicyclohexylcarbodiimide in Combination with a Test for Cholinesterase Inhibitors In this example, there is provided a method for detecting the presence of alkyloxy methylphosphonic acids. In a positive test, a dehydrating agent, 1,3-dicyclohexylcarbodiimide, reacts with an alkyloxy methylphosphonic acid (a non-inhibitor) in the sample causing elimination of a molecule of water from two molecules of the acid and results in the formation of an acid anhydride or "pyro-acid" (a cholinesterase inhibitor). The nerve agent ticket from the U.S. Army M-272 Detector Kit for Waterborne Chemical Agents is then used to determine if a cholinesterase inhibitor was formed in the reaction. This is done by first running a control (analyte level=0), then the analyte sample solution, and comparing the results of the two tests. In each test the enzyme disc is observed immediately after the enzyme disc is separated from the substrate disc. When the test is performed with the control, much or all of the enzyme disc becomes blue. A positive test for a cholinesterase inhibitor is indicated when the enzyme disc of the M-272 detector ticket performed with the analyte sample solution is either completely white or contains more white area than the control.

When this test is used, the interest is mainly in determining if the level of analyte present in the sample unknown exceeds the lower limit of detection of the test. While it may be possible to quantify the level of analyte present in the sample unknown by instrumentally measuring and comparing the amount of blue color produced in the enzyme discs after running the analyte sample solution and the control, only a qualitative result (go/no-go interpretation) is necessary in preferred aspects of the invention, i.e. when the test is used in Chemical Weapons Convention inspections.

The preferred solvent for carrying out this test is acetone while the preferred solid support is Silica Gel IB, Flexible Sheets for Thin Layer Chromatography, Cat. #4462-02, J.T. Baker, Inc., Phillipsburg, N.J. 08865.

A factor limiting the detection sensitivity of this test is that 1,3-dicyclohexylcarbodiimide is a weak cholinesterase inhibitor (or it denatures the enzyme and hence behaves like a weak cholinesterase inhibitor). Thus, the cholinesterase disc obtained with the control (analyte level=0) contains a white spot. Therefore, it is anticipated that the detection sensitivity of this test can be improved significantly if: (a) a dehydrating agent that does not have an adverse effect on the enzyme is used in place of 1,3-dicyclohexylcarbodiimide, or (b) the 1,3-dicyclohexylcarbodiimide is separated from the product of the reaction prior to testing the product of the reaction for anticholinesterase activity. 1,3-Dicyclohexylcarbodiimide can easily be separated from the product of the reaction by eluting the thin-layer chromatography plate (the solid support on which the test is carried out) with a solvent such as dichloromethane. When the latter procedure is used, the control (analyte level=0) is entirely blue. Therefore, when the analyte sample solution is tested, any white spot in the enzyme disc would indicate that a cholinesterase inhibitor was present. Hence, detection sensitivity would be improved substantially compared with tests carried out without the special procedure that removes the 1,3-dicyclohexylcarbodiimide.

Since the M-272 Ticket Test for Nerve Agents is a test for the presence of cholinesterase inhibitors, it can be used to determine if the sample solution contains a cholinesterase inhibitor (e.g. a nerve agent) prior to conducting the test for the presence of alkyloxy methylphosphonic acids. Furthermore, it should be understood that by including the step that is used in all of the microspot tests whereby the analyte is concentrated in a small spot on a sorbent coated plate when the sample solution is applied by capillary action to the sorbent coating using a microcap, the sensitivity of detection of the analyte (a nerve agent or other cholinesterase inhibitor) will be improved substantially compared with the results an otherwise identical test procedure that does not include the additional step.

Analytes Detectable

Ethyl methylphosphonic acid (EMPA), isopropyl methylphosphonic acid (IMPA), pinacolyl methylphosphonic acid (PMPA), cyclohexyl methylphosphonic acid (CMPA), O-ethyl methylphosphonothioic acid (EMPTA) as well as other alkyloxy methylphosphonic acids and alkyloxy methylphosphonothioic acids.

Detection of CWC Analytes

EMPA and IMPA can be detected at the 100 ng level (i.e. when a 1-microliter aliquot of an acetone solution containing 0.01% or more of the analyte is spotted on the solid support using a microcap).

EMPTA and CMPA can be detected at the 1 microgram level (i.e., when a 1-microliter aliquot of an acetone solution containing 0.1% or more of analyte is spotted on the solid support using a microcap).

PMPA can be detected at the 40 microgram level (i.e. when four 1-microliter aliquots of an acetone solution containing 1% or more of the analyte is spotted on the solid support using a microcap).

The detection sensitivity of this test is affected by temperature. When the test is carried out, the temperature of the test is controlled by holding the ticket in the fist while the detection reactions are carried out. Alternatively, if the temperature is controlled using a constant temperature bath, the test temperature can be decreased and the detection sensitivity of the test can probably be improved significantly.

Equipment and Materials a. Locking Forceps or Spotting Bulb Assembly for holding microcap.
b. Microcap, 1-microliter
c. Dropping bottle, 3-mil capacity
d. Syringe, 10-microliter (e.g. cat. #7681B52, Thomas Scientific, Boston, Mass.)
e. 1,3-Dicyclohexylcarbodiimide (1.0 M solution in dichloromethane) (e.g. cat. #37911, Aldrich Chemical Co., Milwaukee, Wis. 53233).
f. Silica Gel IB, Flexible Sheets for Thin Layer Chromatography, Cat. #4462-02, J.T. Baker, Inc., Phillipsburg, N.J. 08865.
g. Nerve Agent Detector Ticket, Water Testing Kit, Chemical Agents, M-272, NSN 6665-01-134-0885.
h. Scissors
i. Pencil Procedure 1. Cut the solid support to size (¼ inch square) and put a dot near the center of the support with a pencil.
2. Lock a 1-microliter microcap in the tip of the locking forceps.
3. Place tip of microcap in a sample of pure acetone and wait a few seconds for the solvent to be drawn by capillary action to fill the microcap.
4a. Place the tip of the microcap in contact with the silica gel surface of a 0.25 inch×0.25 inch piece of solid support at a point on the support that was previously marked with a pencil. Observe the solid support to insure that the liquid leaves the microcap and produces a visible wet spot. Allow a few seconds for the solvent to evaporate. This is the control (analyte level=0).
4b. (The entire test should be repeated using this step only when the test performed with the analyte sample solution and the procedure that includes step 4a does not give a positive test). Repeat the spotting procedure four times, each time using a 1-microliter aliquot of acetone. Observe the solid support to insure that the liquid leaves the microcap and produces a visible wet spot after each application. Allow the solvent to evaporate after each application. This is the control (analyte level=0).
5. Using the syringe, withdraw 2 microliters (4 microliters if 4 microliters of analyte solution is used) of the carbodiimide solution from the septum-sealed bottle and add it to the sample that was spotted on the solid support. Allow the reaction to proceed for the required length of time (3 minutes).
6. Run the Enzyme Ticket Test (see below).
7. Repeat steps 1–6 using the sample solution (acetone solution containing the sample) instead of pure acetone.

Enzyme Ticket Test

1. Remove the M-272 Kit Nerve Agent Detector Ticket from its package. Fold back the silver foil and wet the white (enzyme) disc with a drop of water from a 3-ml dropping bottle.
2. Place the 0.25 inch×0.25 inch section of the solid support that is to be tested for anticholinesterase activity on the enzyme disc. The solid support should be placed on the enzyme disc so that the analyte spot comes in contact with the center of the disc.
3. Cover the solid support with the foil and attach the metal clip to insure and maintain contact of the enzyme disc with the analyte spot. Hold ticket in fist for 3 minutes (for temperature control).
4. Remove the clip, fold back the foil, and then remove and discard the ¼ inch square piece of solid support. Pull the silver foil to completely remove it from the ticket, thereby exposing the substrate disc.
5. Re-wet the enzyme (white) disc with a drop of water and fold the ticket so that the enzyme disc and the substrate disc are in contact with each other.
6. Clip the ticket and hold in fist for 3 minutes (for temperature control).
7. Remove the clip and observe the color of the enzyme disc. [When the test is performed with the control [analyte level=0], much or all of the enzyme disc becomes blue. If the test performed with the sample solution is positive, the enzyme disc from the test will either be completely white or will contain more white area than the enzyme disc from the test with the control].

Purpose and Applications

This micro spot test method can be used as a field screening test for alkyloxy methylphosphonic acids. The test provides evidence for or against the presence of CWC analytes in a sample unknown. This test can be used alone or in conjunction with other micro spot tests that detect other functional groups in a sample unknown. When two or more tests that have different interference profiles are used in combination, the detection specificity for the analyte is increased compared with the result of a single test.

EXAMPLE 6

Micro Spot Test for Methylphosphonic Acid and Methylphosphonofluoridic Acid Using Sodium Carbonate, Diethyl Sulfate, and 1.3-Dicyclohexylcarbodiimide and then the M-272 Detector Kit Ticket for Cholinesterase Inhibitors Methylphosphonic acid and methylphosphonofluoridic acid need to be converted into cholinesterase inhibitors in order to obtain positive tests. This is accomplished by reacting the sample unknown with (1) sodium carbonate, (2) diethyl sulfate, (3) hydrochloric acid (vapor), and (4) 1,3-dicyclohexylcarbodiimide.

A factor limiting the detection sensitivity of this test is that 1,3-dicyclohexylcarbodiimide is a weak cholinesterase inhibitor (or it denatures the enzyme and hence behaves like a weak cholinesterase inhibitor) and hence, the "control" (analyte level=0) contains a white spot. Therefore, it is anticipated that the detection sensitivity of this test can be improved significantly if: (a) a dehydrating agent that does not have an adverse effect on the enzyme is used in place of 1,3-dicyclohexylcarbodiimide, or (b) the 1,3-dicyclohexylcarbodiimide is separated from the product of the reaction prior to testing the product of the reaction for anticholinesterase activity. 1,3-Dicyclohexylcarbodiimide can easily be separated from the product of the reaction by eluting the thin-layer chromatography plate (the solid support on which the test is carried out) with a solvent such as dichloromethane. When the later procedure is used the control (analyte level=0) is entirely blue. Therefore, when the analyte sample solution is tested, any white spot in the enzyme disc would indicate that a cholinesterase inhibitor was present. Hence, detection sensitivity would be improved substantially compared with tests carried out without the special procedure that removes the 1,3-dicyclohexylcarbodiimide from the vicinity of the analyte spot.

Detection Principle (1) Methylphosphonic acid is converted into its sodium salt by reacting it with sodium carbonate. (2) The sodium salt of ethyl methylphosphonic acid is then formed by reacting the sodium salt of methylphosphonic acid with diethyl sulfate. (3) The product of reaction 2 is acidified. (4) A dehydrating reagent 1,3-dicyclohexylcarbodiimide, is then reacted with the alkyloxy methylphosphonic acid causing the formation of an acid anhydride or "pyro-acid" (a cholinesterase inhibitor). The nerve agent ticket from the U.S. Army M-272 Detector Kit for Waterborne Chemical Agents is then used to determine if a cholinesterase inhibitor was formed in the reaction. In a positive test, the enzyme disc on the M-272- ticket is either completely white, or contains more white area than the control, indicating that the cholinesterase was inhibited. The first two reactions probably will result in a cholinesterase inhibitor being formed if the analyte contains methylphosphonofluoridic acid. The last two reactions (with hydrochloric acid and then with 1,3-dicyclohexylcarbodiimide) probably are not needed to obtain a positive test when the analyte is methylphosphonofluoridic acid, but they should not interfere with the test.

Solvent for the Analyte:
An organic solvent (e.g. acetone).
Preferred Solid Support for the Test:
$C_{18}$ Reversed Phase TLC Plates (e.g. cat. #4803-110 MKC18F Reversed Phase Plates, 200 micron thickness, Whatman Chemical Separation Division, Clifton, N.J. 07014).
Analyte Detectable
Methylphosphonic acid (MPA)
Equipment and Materials
Most of the equipment from Example 5 was used in this Example as well. However, the following ingredients were also used:
Sodium carbonate (e.g. cat. #20,442-0, Aldrich Chemical Co.),
Diethyl sulfate (e.g. cat #D10,070-6, Aldrich Chemical Co.),
Hydrochloric Acid (concentrated), and
the following adsorbent coated TLC Plate was used:
$C_{18}$ Reversed Phase TLC Plates (e.g. cat. #4803-110 MK $C_{18}F$ Reversed Phase Plates, 200 micron thickness, Whatman Chemical Separation Division, Clifton, N.J. 07014).

Procedure

1. With a pencil divide the 1 inch×3 inch glass-backed TLC plate into a 1 inch×1 inch section and a 1 inch×two inch section. Use only the 1 inch×1 inch section in the test. With the pencil, place a mark near the center of the 1 inch by 1 inch section.

2. Lock a 1-microliter microcap in the tip of locking forceps.

3. Place tip of microcap in a sample of pure acetone and wait a few seconds for the solvent to be drawn by the capillary to fill the microcap.

4. Place the tip of the microcap in contact with the adsorbent surface of the 1 inch×1 inch section of the solid support at a point on the support that was previously marked with a pencil. Wait a few seconds for the solvent to evaporate. At the same location, spot the solid support with a second 1-microliter quantity of acetone. This is the control (analyte level=0) spot.

5. Allow a few seconds for the solvent to evaporate.

6. Add one drop of 1% aqueous solution of sodium carbonate solution from a dropping bottle to the area of the solid support marked with a pencil. Wait for 1 minute.

7. Using a 10-microliter syringe, add 1 microliter of diethyl sulfate in dichloromethane solution to the same mark on the solid support.

8. Place the adsorbent surface of the solid support over a 200-ml beaker containing ca. 1 ml of concentrated HCl so that HCl vapors come in contact with the adsorbent coated surface. Allow the HCl vapor to contact the adsorbent on the solid support for 1 minute.

9. Using a syringe, withdraw 2 microliters of the 1,3-dicyclohexylcarbodiimide solution from the septum-sealed bottle and add it to the sample that was spotted on the solid support. Wait 1 minute.

10. Perform a test with the enzyme ticket (see Example 4) to determine if a cholinesterase inhibitor formed as a result of reactions.

11. Repeat steps 1–10 using the acetone solution of the sample unknown instead of pure acetone.

Purpose and Applications

This microspot test method can be used as a field screening test for methylphosphonic acid. The test provides evidence for or against the presence of CWC analytes in a sample unknown. This test can be used alone or in conjunction with other micro spot tests that detect other functional groups in a sample unknown. When two or more tests that have different interference profiles are used in combination, the detection specificity for the analyte is increased compared with the result of a single test.

REFERENCES

Detector Reagents

1. Jungreis, E., Spot Test Analysis: Clinical, Environmental, Forensic, and Geochemical Applications, Chemical Analysis, Volume 141, Second Edition, John Wiley and Sons, Inc., N.Y., 1997.
2. Mohammad, A., and Tiwari, S., Thirty-Five Years of Thin-Layer Chromatography in the Analysis of Inorganic Anions, Separation Science and Technology, 30(19), 3577–3614 (1995).
3. Jork, Helmut, Editor, Thin-Layer Chromatography: Reagents and Detection Methods, Vol. 1b, Physical and Chemical Detection Methods, John Wiley & Sons, N.Y., 1994.
4. Green, F. J., The Sigma Aldrich Handbook of Stains, Dyes, and Indicators, Aldrich Chemical Co., 1990.
5. Novak, T. J., and Davis, P. M., Detection of Sulfur Mustards Using Spectrofluorometry, U.S. Pat. No. 5,032,380, Jul. 16, 1991.
6. Jork, Helmut, Editor, Thin-Layer Chromatography: Reagents and Detection Methods, Vol. 1a, Physical and Chemical Detection Methods, John Wiley & Sons, N.Y., 1989.
7. Novak, T. J., 4,4'-Dithiodianil, U.S. Pat. No. 4,414,414, Nov. 8, 1983.
8. Sherma, J., Practice and Applications of Thin Layer Chromatography on Whatman $KC_{18}$ Reversed Phase Plates, TLC Technical Series, Volume 1 (1981), Whatman Inc., Clifton, N.J. 07014.
9. Sass, S., and Ludemann, W., J. of Chromatography, 187, 447–452 (1980).
10. Gasparic, J., and Churacek, J., Detection Reagents, Laboratory Handbook of Paper and Thin Layer Chromatography, pp 323–335, Ellis Horwood, Ltd, England, 1978.
11. Corporate Authors, E. Merck, Dyeing Reagents for Thin Layer and Paper Chromatography, E. Merck, Darmstadt, Federal Republic of Germany, 1975.
12. Corporate Authors, Eastman Kodak Company, Eastman TLC Visualization Reagents and Chromatographic Solvents, Kodak Publication No. JJ-5 (1973), Eastman Kodak Company, Rochester, N.Y. 14650.
13. Zweig, G., and Sherma, J., Editors, Detection Reagents for Paper and Thin-Layer Chromatography, CRC Handbook of Chromatography, Volume II, Section II.I, pp 103–189, CRC Press, 1972.
14. Sawicki, E., Engel, C. R., and Elbert, W. C., Talanta 14, 1169–1178 (1967).
15. Ruch, W. E., Editor, Chemical Detection of Gaseous Pollutants: An Annotated Bibliography, Ann Arbor Science Publishers, Inc., Ann Arbor, Mich., 1966.
16. Feigl, F., Spot Tests in Organic Analysis, 6th Edition, Elsevier Science, Ltd., 1966.
17. Bryant, F., Overell, B. T., Biochim et Biophys. Acta 10, 471–6 (1963).
18. Feigl, F., Spot Tests in Inorganic Analysis, 7th Edition, Elsevier Science, Ltd, 1958.
19. Epstein, J., Rosenthal, R. W., and Ess, R. J., Anal. Chem. 27, 1435–39 (1955).
20. Bregoff, H. M., Roberts, E., Delwiche, C. C., J. Biol. Chem. 205, 565 (1953).
21. Munier, R. Bull. Soc. Chim. Biol. 35, 1225 (1953).
22. Obermiller, M., Angew. Chem. 49, 162–164 (1936).
23. Witten, B., and Prostak, A., Sensitive Detector Crayons for Phosgene, Hydrogen Cyanide, and Lewisite, Anal. Chem. 29, 885–7 (1957).
24. Pheil, R. W., Crayon for the Detection of G-Agents, U.S. Pat. No. 2,929,791, Mar. 22, 1960.
25. Sass, S., Ludemann, W. D., Witten, B., Fischer, V., Sisti, A. J., and Miller, J. I., Colorimetric Determination of Certain Organophosphorus Compounds and Acylating Agents—Use of Diisonitrosoacetone Reagent, Anal. Chem. 29, 1346–9 (1957).
26. Kramer, D. N., and Morin, R. D., Detection of G-Agents, U.S. Pat. No. 2,926,072, Feb. 23, 1960.
27. Gehauf, B., Epstein, J., Wilson, G. B., Witten, B., Sass, S., Bauer, V. E., Rueggeberg, W. H. C., Anal. Chem. 29, 276 (1957).
28. Gehauf, B., and Goldenson, J., Detection and Estimation of Nerve Gases by Fluorescence Reaction, Anal. Chem. 29, 276 (1957).
29. Brante, G., Iodine as a Means of Development in Paper Chromatography, Nature 163, 651–2 (1949).
30. Sokolowski, M., and Rozylo, J. K., TLC Analysis of Warfare Agents under Battlefield Conditions, Journal of Planar Chromatography 6, 467–71 (1993).
31. Munavalli, S., and Pannella, M., Thin-Layer Chromatography of Mustard and Its Metablolites, Journal of Chromatog., 437, 423–8 (1988).
32. Ellman, G. H., Arch. Biochem. Biophys., 82, 70–77 (1959).
33. Mikrochim Acta, 788 (1971); Ibid., 341 (1973).
34. Mikrochim Acta, 526 (1972).
35. Chemical and Engineering News, pg 29, Aug. 1, 1994.
36. Yoe, J. H., and Sarver, L. A., Organic Analytical Reagents, John Wiley, N.Y., 1941, pages 66–326.
37. Maile, R. J., Fishesser, G. J., and Anderson, M. M., Thin-Layer Chromatography of Phosphonic Acid Derivatives, Journal of Chromatog. 132, 366–68 (1977).
38. Reiner, M., ed., Standard Methods of Clinical Chemistry, Vol. 1, Academic Press, N.Y., 1953, page 84.
39. T. E. Edmonds, J. M. Lee, and J. D. Lee, Dry Reagent Chemical Tests, Analytical Communications, 34, 1H–3H (1997).
40. A. Zipp, W. E. Hornby, Solid Phase Chemistry: Its Principles And Applications In Clinical Analysis, Talanta31, 863(1984).
41. E. Diebold, M. Rapkin, and A. Usmami, Chemistry On A Stick (Part 1), Chemtech 21, 462 (1991).
42. A. Burke, J. DuBois, A. Azhar, and A. Usmani, Chemistry On A Stick (Part 2), Chemtech 21, 547 (1991).

What is claimed is:

1. A method of detecting the presence of alkyloxy methylphosphonic acid in a sample, comprising the steps of:
   (a) mixing the sample with a dehydrating agent where alkyloxy methylphosphonic acid in the sample reacts with the dehydrating agent to produce a cholinesterase inhibitor; and
   (b) detecting the presence of the cholinesterase inhibitor to indicate the presence of alkyloxy methylphosphonic acid in the sample.

2. The method according to claim 1 wherein the dehydrating agent is selected from the group consisting of 1,3-dicyclohexylcarbodiimide and 1,3-diisopropylcarbodiimide.

3. The method according to claim 1 wherein alkyloxy methylphosphonic acid is selected from the group consisting of ethyl methylphosphonic acid, isopropyl methylphosphonic acid, cyclohexyl methylphosphonic acid and pinacolyl methylphosphonic acid.

4. A method of detecting the presence of alkyloxy methylphosphothioic acid in a sample, comprising the steps of:
(a) mixing the sample with a dehydrating agent where alkyloxy methylphosphothioic acid in the sample reacts with the dehydrating agent to produce a cholinesterase inhibitor; and
(b) detecting the presence of the cholinesterase inhibitor to indicate the presence of alkyloxy methylphosphothioic acid in the sample.

5. The method according to claim 4 wherein the dehydrating agent is selected from the group consisting of 1,3-dicyclohexylcarbodiimide and 1,3-diisopropylcarbodiimide.

6. The method according to claim 4 wherein the alkyloxy methylphosphothioic acid comprises O-ethyl methylphosphonothioic acid.

7. A method of detecting the presence of an alkyloxy methylphosphonic acid in a sample, comprising the steps of:
(a) mixing the sample with an acid chloride and triethylamine where alkyloxy methylphosphonic acid in the sample reacts with the acid chloride and triethylamine to produce a cholinesterase inhibitor; and
(b) detecting the presence of cholinesterase inhibitor in the sample to indicate the presence of alkyloxy methylphosphonic acid in the sample.

8. A method of detecting the presence of methylphosphonic acid in a sample, comprising the steps of:
(a) mixing the sample with an esterification reagent where methylphosphonic acid in the sample reacts with the esterification reagent to produce an alkyloxy methylphosphonic acid,
(b) reacting the alkyloxy methylphosphonic acid formed in the sample with a dehydrating agent so that a cholinesterase inhibitor is produced in the sample; and
(c) detecting the presence of the cholinesterase inhibitor in the sample to indicate the presence of methylphosphonic acid in the sample.

9. The method according to claim 8, wherein the esterification reagent is selected from the group of consisting of dialkyl sulfate and alkyl iodide.

10. The method according to claim 8, wherein the dehydrating agent is selected from the group consisting of 1,3-dicyclohexylcarbodiimide and 1,3-diisopropylcarbodiimide.

11. A method of detecting the presence of a methylphosphonofluoridic acid in a sample, comprising the steps of:
(a) mixing the sample with an esterification reagent where methylphosphonofluoridic acid in the sample reacts with the esterification reagent to produce a cholinesterase inhibitor, and
(b) detecting the presence of the cholinesterase inhibitor to indicate the presence of methylphosphonofluoridic acid in a sample.

12. A method according to claim 11, wherein the esterification reagent is selected from the group consisting of dialkyl sulfate and alkyl iodide.

* * * * *